United States Patent [19]

Porter

[11] 4,031,895
[45] June 28, 1977

[54] SYRINGE ASSEMBLY PACKAGE

[76] Inventor: Robert E. Porter, 1734 Machado St., Oceanside, Calif. 92054

[22] Filed: Apr. 5, 1976

[21] Appl. No.: 674,033

[52] U.S. Cl. .................... 128/272.1; 128/218 M; 206/219
[51] Int. Cl.² .................... A61M 5/18; B65D 81/32
[58] Field of Search .......... 206/365, 366, 364, 370, 206/219, 222; 128/218 M, 218 P, 218 R, 272, 272.1, 272.3

[56] References Cited

UNITED STATES PATENTS

| 2,168,686 | 8/1939 | Saffir | 128/272 |
| 2,666,434 | 1/1954 | Ogle | 128/218 P |
| 3,336,924 | 8/1967 | Sarnoff et al. | 128/272.3 |
| 3,397,694 | 8/1968 | Ogle | 128/272.1 |

*Primary Examiner*—William T. Dixson, Jr.
*Attorney, Agent, or Firm*—Strauch, Nolan, Neale, Nies & Kurz

[57] ABSTRACT

A prepackaged syringe assembly consists of a syringe and a vessel containing respective substances to be mixed at the time of medication to the patient, the vessel being slidably and rotatably mounted in one end of a transparent support tube and the syringe having an offset needle and being slidably detachably mounted in the other end of the tube, and rotation of the vessel between predetermined positions locating a syringe needle sealing body and a puncturable closure element on the inner end of the vessel in alignment with the needle.

11 Claims, 4 Drawing Figures

SYRINGE ASSEMBLY PACKAGE

This invention relates to syringe assemblies and particularly to an improved syringe assembly package of the type wherein a syringe, such as a hypodermic syringe, preloaded with one substance such as a liquid diluent is packaged in assembly with a separate compartment or the like containing another substance such as a dry medication powder to be mixed with the first substance only at about the time the syringe is to be used to administer an injection.

Composite packages of this type have been proposed, as for example that disclosed in U.S. Letters Patent to Sorensen et al No. 3,416,657. In that patent the preloaded syringe has the needle tip initially protected and closed by being imbedded in a body of suitable material such as rubber and the syringe is manipulated to push the needle through the rubber body to discharge its contents into a compartment containing powder or the like to be mixed with the contents of the syringe and then reloaded while still in the package, to charge the syringe with the fluid mixture, after which all of the remaining part of the package is discarded and the reloaded syringe is ready to use to administer an injection to the patient.

While the foregoing patented structure accomplished the desired result, there have been some problems such as possible premature leakage from the syringe into the powder compartment, and the present invention eliminates these problems.

It is therefore the major object of the invention to provide a novel syringe assembly package wherein a preloaded syringe is so incorporated in the package with an isolated compartment device containing a substance to be mixed with the substance in the syringe that there is no risk of premature mixing of the substances and yet the assembly may be rapidly manipulated to mix the substances and store them in the syringe prior to separation of the syringe from the package.

A further object of the invention is to provide a novel package of the foregoing type wherein the syringe is of the kind having a non-concentric needle and the compartment defining device is a special container movable within the package between operative positions where it blocks or permits access of the syringe needle to the interior of the container.

Another more detailed object of the invention is to provide in the foregoing package a special rotatably mounted container having at its inner end a syringe needle closure plug and a sealable access mouth.

PREFERRED EMBODIMENTS

Figure 1:
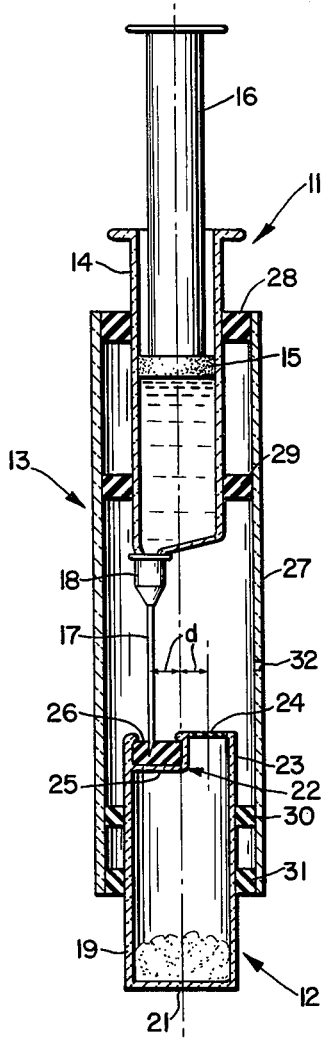
FIG. 1 is a side view mainly in section showing a syringe assembly package according to a preferred embodiment of the invention, with the preloaded syringe and container disposed in initially packaged syringe closing position.

The package of the invention consists essentially of a hypodermic syringe 11, a container 12 and a packaging structure 13 that maintains the syringe and container in operative relative relation after initial assembly and up to the point of use, but permits relative manipulation of the syringe and container while in the package for providing a mixture of the substances in the loaded syringe prior to the separation of the syringe from the package.

Syringe 11 comprises a stiff transparent cylindrical barrel 14 within which is slidably mounted a plunger piston 15 having an external handle 16. The piston 15 defines the movable wall of a chamber for containing a measured amount of one substance as a liquid diluent for the contents of container 12. As shown the syringe needle 17 is mounted on the end of barrel 14 by a fitting 18 so that the longitudinal axis of the needle is parallel but offset relative to the longitudinal axis of barrel 14. Syringes having such non-concentric needles are known, and examples of such are disclosed in U.S. Letters Pat. No. 3,786,811 and 3,819,091. Thus, the syringe 11 may preferably be of a known type having the offset non-concentric needle.

Container 12 has a cylindrical side wall 19, a bottom wall 21 and a top wall 22. As shown wall 22 is of special construction, having an eccentric or offset cylindrical neck 23 that is normally closed as by a diaphragm 24 sealed around its top opening. Diaphragm 24 may be a thin disc of soft rubber or any normally gas tight similar material that may be sealingly attached over the neck opening, may be readily punctured by thrust of the needle 17, and may sealingly surround the introduced needle as will appear.

The top wall of the container is formed with an upwardly open pocket or well 25 within which is secured a body 26 of relatively soft rubber or like substance capable of receiving, imbedding and closing the sharp open end of needle 17 when the parts are in the association of FIG. 1.

The barrel 14 and container side wall 19 may advantageously be coaxial within the package and of about the same external diameter, and the center of the top opening of container neck 23 is preferably offset from the longitudinal central axis of the container a distance $d$ which is equal to the distance that the needle axis is offset from the axis of barrel 14 in the assembly for a purpose to appear.

The package comprises a tubular support structure in the form of a stiff transparent cylindrical tube 27 of glass or plastic having within its upper end two concentric annular rings 28 and 29 coaxially mounting the syringe. Rings 28 and 29 have their outer peripheries fixed to the interior of tube 27 and inner peripheries smoothly frictionally fairly tightly receive barrel 14 to slidably rotatably hold the syringe in the package.

Similar annular rings 30 and 31 are fixed within the lower end of tube 27 and slidably and rotatably frictionally mount the container 12 which may be a smooth walled glass or plastic bottle.

The side wall of tube 27 has at least one opening 32 to prevent air compression from blocking relative sliding movement of the container and syringe.

FIG. 1 shows the package as initially assembled in the laboratory or factory. Usually the syringe barrel is held more firmly than the container against longitudinal movement in the package, but in any event the container is oriented to align body 26 to imbed therein the end of needle 17 as shown in FIG. 1.

Figure 2:
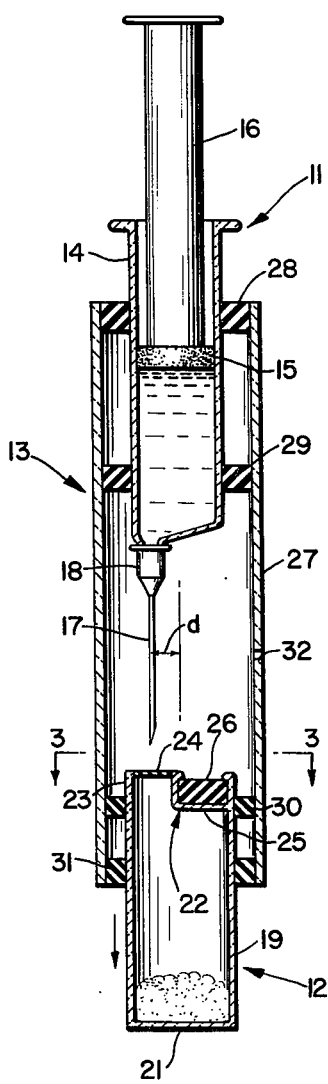
FIG. 2 is a side elevation similar to FIG. 1 but showing the container moved to mixing access position while remaining in the package.

When it is desired to use the medication, container 12 is pulled downwardly to free the tip of needle 17 from body 26 and rotated 180° about its axis to the approximate position illustrated in FIG. 2 wherein diaphragm 24 is aligned with needle 17.

Figure 4:
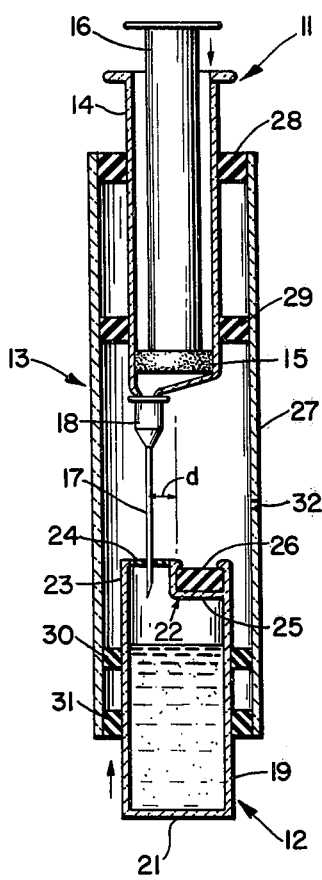
FIG. 4 is a side elevation similar to FIGS. 1 and 2, but showing the container moved to the position where the substance within the syringe and container may be mixed and the syringe reloaded in the package.
Figure 3:
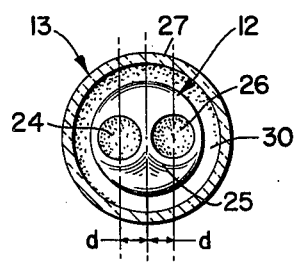
FIG. 3 is a section substantially on line 3—3 in FIG. 2.

Now the container is pushed upwardly to thrust the tip of needle 17 through diaphragm 24 into the interior of container 12 in the approximate position illustrated in FIG. 4. The syringe plunger is now pushed down as shown in FIG. 4 to discharge the liquid into container 12 where it mixes with the contents of the container as shown in FIG. 4.

The syringe piston is now manipulated to the aproximate position of FIGS. 1 and 2, drawing into the barrel the medication mixture from container 12, and then the syringe barrel is pulled entirely out of the tube 27 ready for immediate use in administering an injection to a patient.

While it is preferred as above described to maintain the syringe barrel against longitudinal movement relative to tube 27 until final separation, it will be appreciated that in some packages the syringe barrel and container may be otherwise relatively slidably displaced and rotated for the same result. In some forms the container may be fixed and only the syringe rotated.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A prepackaged syringe assembly comprising a support structure, a syringe having a discharge needle and a barrel adapted to be loaded with a first substance and a container adapted to be loaded with a second substance, said syringe and said container being mounted in said structure for relative slidable and rotational displacement, said syringe having its needle tip within said structure and said container mounting within the structure a sealing body wherein the needle tip is imbedded in one relative position of rotation of said syringe and container for isolation of said substances while in the structure and also mounting a puncturable closure element laterally spaced from said sealing body adapted to permit entry of the needle tip into the container in another relative position of rotation of the syringe and container in the package for admixture of said substances and reloading of the syringe with the mixture, said syringe being separable from the remainder of the assembly for immediate use after said reloading.

2. The syringe assembly defined in claim 1 wherein said syringe has its barrel axially slidably mounted in said structure, and said container is a vessel axially slidably mounted in said structure and rotatable about its axis for disposing either said sealing body or said closure element in substantial alignment with said syringe needle.

3. The syringe assembly defined in claim 1, wherein said syringe is of the type having its needle offset relative to the axis of its barrel and said container is a vessel having on its inner end in the package an access opening over which said element is disposed and adjacent means mounting said sealing body.

4. The syringe assembly defined in claim 1, wherein said support structure is a tubular member and said syringe and container are mounted to project from opposite ends of said member for effecting said relative displacement.

5. The syringe defined in claim 4, wherein said container is a vessel that is rotatably and axially slidably mounted at one end of said member, and the syringe barrel is slidably detachably mounted in the other end of said member.

6. The syringe assembly defined in claim 5, wherein said syringe barrel and vessel are coaxial, the syringe needle is offset from the axis of its barrel and the sealing body and closure element are mounted on the inner end of said vessel in such relation as to dispose one or the other in operative alignment with said needle upon predetermined rotation of said vessel about its axis.

7. The syringe assembly defined in claim 6, wherein said tubular member is a transparent tube.

8. The syringe assembly defined in claim 6, wherein said syringe barrel and the container are cylindrical and of the same diameter, and said closure member and sealing body are disposed at about equal distances from the axis of rotation of the container.

9. The syringe defined in claim 6, wherein the inner end of said container is formed with a well in which said sealing body is mounted and a discharge neck over which said closure element is initially sealed.

10. A prepackaged syringe assembly comprising a support structure, a syringe having a discharge needle and a barrel adapted to be loaded with a first substance and a container adapted to be loaded with a second substance mounted in said structure for relative slidable and rotational displacement, said syringe having its needle tip within said structure and said container mounting within the structure a sealing body adapted to receive and imbed the needle tip in one relative location of said syringe and container for isolation of said substances while in the structure and a puncturable closure element adapted to permit entry of the needle tip into the container in another relative position of the syringe and container in the package for admixture of said substances and reloading of the syringe with the mixture, said syringe being separable from the remainder of the assembly for immediate use after said reloading, said syringe being of the type having its needle offset relative to the axis of its barrel and said container being a vessel having on its inner end in the package an access opening over which said closure element is disposed and adjacent means mounting said sealing body.

11. The syringe assembly defined in claim 10, wherein said syringe barrel and vessel are cylindrical and coaxial, and said elment and sealing body are located at substantially equal distances from that common axis.

* * * * *